US006890554B2

(12) United States Patent
Jessee et al.

(10) Patent No.: US 6,890,554 B2
(45) Date of Patent: May 10, 2005

(54) GENETIC IMMUNIZATION WITH CATIONIC LIPIDS

(75) Inventors: Joel A. Jessee, Mt. Airy, MD (US); William G. Hearl, Columbia, MD (US)

(73) Assignee: Invitrogen Corporation, Carlsbad, CA (US)

( * ) Notice: Subject to any disclaimer, the term of this patent is extended or adjusted under 35 U.S.C. 154(b) by 163 days.

(21) Appl. No.: 08/450,555

(22) Filed: May 25, 1995

(65) Prior Publication Data

US 2002/0077305 A1 Jun. 20, 2002

Related U.S. Application Data

(63) Continuation of application No. 08/069,720, filed on Jun. 1, 1993, now abandoned.

(51) Int. Cl.⁷ .............................................. A61K 9/127
(52) U.S. Cl. ..................... 424/450; 435/320.1; 435/455; 435/458; 514/44; 424/130.1
(58) Field of Search .............................. 424/450, 130.1; 435/320.1, 455, 458, 326; 514/44

(56) References Cited

U.S. PATENT DOCUMENTS

| | | | |
|---|---|---|---|
| 4,224,404 A | | 9/1980 | Viza et al. |
| 4,394,448 A | | 7/1983 | Szoka, Jr. et al. |
| 4,806,463 A | | 2/1989 | Goodchild et al. |
| 4,897,355 A | | 1/1990 | Eppstein et al. ......... 435/240.2 |
| 4,946,787 A | | 8/1990 | Eppstein et al. ......... 435/240.2 |
| 5,049,386 A | | 9/1991 | Eppstein et al. ............ 424/427 |
| 5,166,320 A | * | 11/1992 | Wu et al. .................... 530/395 |
| 5,171,678 A | * | 12/1992 | Behr et al. ............... 435/172.3 |
| 5,208,036 A | | 5/1993 | Eppstein et al. ............ 424/450 |
| 5,264,618 A | | 11/1993 | Felgner et al. |
| 5,283,185 A | * | 2/1994 | Epand et al. ............... 435/455 |
| 5,328,470 A | * | 7/1994 | Nabel et al. ................ 604/101 |
| 5,334,761 A | * | 8/1994 | Gebeyehu et al. .......... 564/197 |
| 5,459,127 A | | 10/1995 | Felgner et al. |
| 5,580,859 A | | 12/1996 | Felgner et al. ................ 514/44 |
| 5,589,466 A | | 12/1996 | Felgner et al. ................ 514/44 |
| 5,593,972 A | | 1/1997 | Weiner et al. ................ 514/44 |
| 5,641,662 A | | 6/1997 | Debs et al. ............... 435/172.1 |
| 5,676,954 A | * | 10/1997 | Brigham ..................... 424/450 |
| 5,691,460 A | * | 11/1997 | Duvic et al. |
| 5,693,622 A | | 12/1997 | Wolff et al. |
| 5,703,055 A | | 12/1997 | Felgner et al. ................ 514/44 |
| 5,726,298 A | * | 3/1998 | Hirai et al. |
| 5,756,353 A | * | 5/1998 | Debs .......................... 435/375 |
| 5,780,053 A | | 7/1998 | Ashley et al. .............. 424/450 |
| 5,827,703 A | * | 10/1998 | Debs et al. ................. 435/455 |
| 5,908,635 A | | 6/1999 | Thierry ....................... 424/450 |
| 5,908,777 A | | 6/1999 | Lee et al. ................. 435/320.1 |
| 6,030,626 A | * | 2/2000 | Kolattukudy et al. .... 424/256.1 |
| 6,103,492 A | * | 8/2000 | Yu |
| 6,110,662 A | * | 8/2000 | Foung et al. ................... 435/5 |
| 6,214,804 B1 | * | 4/2001 | Felgner ........................ 515/44 |
| 6,228,844 B1 | | 5/2001 | Wolff et al. |
| 6,251,390 B1 | * | 6/2001 | Harman .................... 424/94.61 |
| 6,387,395 B1 | | 5/2002 | Eppstein et al. ............ 424/450 |
| 6,413,942 B1 | | 7/2002 | Felgner et al. |
| 2002/0086849 A1 | | 7/2002 | Gebeyehu et al. |
| 2003/0032615 A1 | | 2/2003 | Felgner et al. |
| 2003/0186913 A1 | | 10/2003 | Wolff et al. |

FOREIGN PATENT DOCUMENTS

| | | |
|---|---|---|
| EP | 0 465 529 | 4/1998 |
| EP | 0 523 189 | 6/1999 |
| EP | 1 026 253 | 8/2000 |
| EP | 0 737 750 | 5/2003 |
| WO | WO88/05077 | 7/1988 |
| WO | WO90/01543 | 2/1990 |
| WO | WO 90/11092 | 10/1990 |
| WO | WO 91/15501 | 10/1991 |
| WO | WO 91/16024 | 10/1991 |
| WO | WO91/16024 | 10/1991 |
| WO | WO91/17424 | 11/1991 |
| WO | WO 91/17424 | 11/1991 |
| WO | WO 93/03709 | 3/1993 |
| WO | WO 94/05624 | 3/1994 |

OTHER PUBLICATIONS

US 2002/0198163,, 12/2002, Felgner et al. (withdrawn)
Gao et al. (Biochim. Biophys. Res. Comm. 179:280–285, 1991).*
Crystal, Science, vol. 270, 404–410 (1995).*
Robert Whalen, Emerging Infections Diseases, vol. w, 3:168–175 (1996).*
Zephati et al., J. Controlled Release, 1996, 41:97–119.*
PL Felgner et al (1991) Nature 349:351–352.*
Ciccarone, V. et al., "Cationic Liposome–Mediated Transfection of Eukaryotic Cells: High Efficiency Nucleic Acid Delivery With Lipofectin, Lipofectace, And Lipofectamine Reagents," FASEB J. 7:A1131 Abstract No. 454 (Apr. 1993).*
Rosenthal, A.F. et al., A Synthetic Inhibitor of Venom Lecithinase A, Journal of Biological Chemistry 235: 2202–2206 (Aug. 1960).
Tang, D. et al., Genetic immunization is a simple method for eliciting an immune response, Nature 356: 152–154 (Mar. 12, 1992).
Thompson, L. "A Shot in the Arm for Vaccine Problems" Washington Post, p. A03 (Jun. 7, 1993).
Behr, J. et al., Efficient gene transfer into mammalian primary endocrine cells with lipopolyamine–coated DNA, Proceedings of the National Academy of Science 86: 6982–6986 (Sep. 1989).
Benoist, C. et al., In vivo sequence requirements of the SV40 early promoter region, Nature 290: 304–310 (Mar. 26, 1981).

(Continued)

Primary Examiner—Dave T. Nguyen
(74) Attorney, Agent, or Firm—Greenlee, Winner and Sullivan, P.C.

(57) ABSTRACT

A method for immunization using genetic material is disclosed. Compositions for genetic immunization comprising cationic lipids and polynucleotides are also disclosed. Methods for using genetic immunization to produce polyclonal and monoclonal antibodies are also disclosed. A method for epitope mapping is also disclosed.

19 Claims, No Drawings

OTHER PUBLICATIONS

Cohen, J., Naked DNA Points Way to Vaccines, *Science 259*: 1691–1692 (Mar. 19, 1993).

Düzgünes, N. et al., Fusion of Liposomes Containing a Novel Cationic Lipid, N-[2,3-(Dioleyloxy)propyl]-N,N, N-trimethylammonium: Induction by Multivalent Anions and Asymmetric Fusion with Acidic Phospholipid Vesicles, *Biochemistry 28*: 9179–9184 (1989).

Felgner, P.L. et al., Cationic Liposome–Mediated Transfection, *Focus 11*: 21–25 (Spring 1989).

Felgner, P.L. et al., Cationic liposome–mediated transfection, *Nature 337*: 387–388 (Jan. 26, 1989).

Felgner, P.L. et al., Lipofection: A highly efficient, lipidmediated DNA–transfection procedure, *Proceedings of the National Academy of Science 84*: 7413–7417 (Nov. 1987).

Foecking, M.K. et al., Powerful and versatile enhancer–promoter unit for mammalian expression vectors, *Gene 45*: 101–105 (1986).

Gao, X. et al., A novel cationic liposome reagent for efficient transfection of mammalian cells, *Biochem. Biophys. Res. Commun. 179*: 280–285 (Aug. 30, 1991).

Gorman, C. et al., "High Efficiency Gene Transfer into Mammalian Cells" in Glover, D.M., ed., *DNA Cloning*, vol. II, IRL Press, Washington, D.C. pp. 143–190 (1985).

Hazinski, T.A. et al., Localization and Induced Expression of Fusion Genes in the Rat Lung, *Am. J. Respir. Cell Mol. Biol. 4*: 206–209 (1991).

Holt, C.E. et al., Lipofection of cDNAs in the Embryonic Vertebrate Central Nervous System, *Neuron 4*: 203–214 (Feb. 1990).

Benvenisty et al. (1986), "Direct introduction of genes into rats and expression of the genes," Proc. Natl. Acad. Sci. 83:9551–9555.

Cotten, M. and Wagner, E. (1993), "Non–viral approaches to gene therapy," Curr. Opinion Biotechnol. 4:705–710.

Dubensky et al. (1984), "Direct transfection of viral and plasmid DNA into the liver or spleen of mice," Proc. Natl. Acad. Sci. 81:7529–7533.

Felgner, P.L. and Rhodes, G. (1991), "Gene Therapeutics," Nature 349:351–352.

Felgner, P.L. and Ringold, G.M. (1989), "Cationic Liposome–Mediated Transfection," Nature 337:387–388.

Felgner et al. (1987), "Lipofection: A highly efficient, lipid–mediated DNA–transfection procedure," Proc. Natl. Acad. Sci. 84:7413–7417.

Litzinger, D.C. and Huang, L. (1992), "Phosphatidylethanolamine liposomes: drug delivery, gene transfer and immunodiagnostic applications," Biochim. Biophys. Acta 1113:201–227.

Loyter et al. (1982), "Mechanisms of DNA uptake by mammalian cells: Fate of exogeneously added DNA monitored by the use of fluorescent dyes," Proc. Natl. Acad. Sci. 79:422–426.

Malone et al. (1989), "Cationic liposome–mediated RNA transfection," Proc. Natl. Acad. Sci. 86:6077–6081.

Mannino, R. and Gould–Fogerite, S. (1988), "Liposome Mediated Gene Transfer," BioTechniques 6(7):682–690.

Nabel, G.J. and Felgner, P.L. (1993), "Direct gene transfer for immunotherapy and immunization," TIBTECH 11:211–215.

Nicolau et al. (1983), "In Vivo expression of rat insulin after intravenous administration of the lipsome–entrapped gene for rat insulin I," Proc. Natl. Acad. Sci. 80:1068–1072.

Nicolau, C. et al. (1987), "Liposomes as Carriers for in Vivo Gene Transfer and Expression," Methods Enzymol. 149:157–176.

Rhodes, G. et al. (1990), "Intramuscular injection of an expression vector containing the gene for HIV GP 120 induces antibodies to the GP 120 protein," Sixth Intl. Conf. on Aids, San Francisco, (Jun. 20–21, 1990), vol. 2 Abstracts, Abstract 1048.

Selden et al. (1988), "Expression of the human growth hormone variant gene in cultured fibroblasts and transgenic mice," Proc. Natl. Acad. Sci. 85:8241–8245.

Wolff, J.A. et al. (1990), "Direct gene transfer into mouse muscle in vivo," Science 247:1465–1468.

Wu, C.H. et al. (1989), "Targeting Genes: Delivery and Persistent Expression of a Foreign Gene Driven by Mammalian Regulatory Elements in Vivo," J. Biol. Chem. 264(29):16985–16987.

Johnstone & Thorpe, "Production of antibodies," in: *Immunochemistry in Practice*, published by Blackwell Scientific Publications (Oxford), pp. 30–47 (1987).

Neurath et al., "B cell epitope mapping of human immunodeficiency virus envelope glycoproteins with long (19– to 36–residue) synthetic peptides," *J. Gen. Virol. 71*: 85–95 (1990).

Ulmer, J.B. et al., Heterologous Protection Against Influenza by Injection of DNA Encoding a Viral Protein, *Science 259*: 1745–1749 (Mar. 19, 1993).

Wang, B. et al., Gene inoculation generates immune responses against human immunodeficiency virus type 1, *Proceedings of the National Academy of Science 90*: 4156–4160 (May 1993).

Zhou, X. et al., Lipophilic polylysines mediate efficient DNA transfection in mammalian cells, *Biochimica et Biophysica Acta 1065*: 8–14 (1991).

* cited by examiner

GENETIC IMMUNIZATION WITH CATIONIC LIPIDS

This application is a continuation of application Ser. No. 08/069,720, filed Jun. 1, 1993, now abandoned.

FIELD OF THE INVENTION

The present invention is in the field of immunology. In particular, this invention is directed to methods of immunization using compositions comprising cationic lipids and polynucleotide molecules which code for immunogens. This invention is also directed to methods for producing polyclonal and monoclonal antibodies from genetically immunized animals. This invention is further directed to the use of genetic immunization to map protein epitopes.

BACKGROUND OF THE INVENTION

Traditional methods of immunization are achieved by injection of a mixture of antibodies which immunoreact with an invading pathogen (i.e., passive immunization), or by vaccination, which stimulates the immune system to produce pathogen-specific antibodies. Since foreign antibodies are cleared by the recipient, passive immunity confers only temporary protection. Vaccination confers longer-lasting active immunity.

In order to be effective, vaccination must generate humoral and/or cell-mediated immunity which will prevent the development of disease upon subsequent exposure to the corresponding pathogen. The pertinent antigenic determinants must be presented to the immune system in a manner that mimics a natural infection. Conventional viral vaccines may consist of inactivated virulent strains, or live-attenuated strains (Old et al., *Principles of Gene Manipulation: An Introduction to Genetic Engineering*, Blackwell Scientific Publications, 4th edition, 1989). A general problem with using a vaccine consisting of a virus is that many viruses (such as hepatitis B virus) have not been adapted to grow to high titre in tissue culture and thus, cannot be produced in sufficient quantity (Id.). In addition, the use of inactivated viruses present a potential danger of vaccine-related disease resulting from replication-competent virus may remain in the inoculum. Outbreaks of foot-and-mouth disease in Europe have been attributed to this cause (Id.). On the other hand, attenuated virus strains have the potential to revert to virulent phenotype upon replication in the vaccinee. This problem has been reported to occur about once or twice in every million people who receive live polio vaccine (Id.). Moreover, encephalitis can occur following measles immunization with attenuated virus (Roit, I. M. *Essential Immunology*, Blackwell Scientific Publications, Sixth Ed., 1988). Another disadvantage of using attenuated strains is the difficulty and expense of maintaining appropriate cold storage facilities (Id.). A major disadvantage associated with the use of live virus vaccines is that persons with congenital or acquired immunodeficiency risk severe infections. Such persons include children in developing countries who are often immunodeficient because of malnutrition and/or infection with viruses or parasites (Id., Old et al., supra).

As a result of recent advances in molecular biology and peptide synthesis, it is possible to produce purified viral proteins or synthetic peptides for use in immunoprophylaxis (Murphy et al., "Immunization Against Viruses," in *Virology*, Fields et al., Eds., Raven Press, New York, pp. 349–370, 1985). Purified antigens may be produced by synthesizing peptides which represent immunologically important domains of surface antigens of the pathogen. The synthetic peptide approach has been successfully used with an antigenic determinant of the foot and mouth disease virus (Id.). One problem with this approach is that the poor antigenicity of synthetic peptides has required the use of Freund's adjuvant to enhance the immune response in experimental animals (Id.). Since Freund's adjuvant cannot be used in humans, an effective adjuvant for human use must be developed (Id.). In addition, a single antigenic site may not be sufficient to induce resistance since large surface antigens usually contain several distinct immunological domains that elicit a protective humoral and/or cell-mediated response (Braciale et al., *J. Exp. Med.* 153:910–923 (1981); Wiley et al., *Nature* 289:373–378 (1981)). There may also be difficulties in stimulating an immunologic response to epitopes that are formed by non-contiguous parts of the linear protein molecule (Murphy, et al., supra). There is evidence that the majority of protein determinants are discontinuous and involve amino acid residues that are far apart in the primary amino acid sequence, but are brought into close juxtaposition by peptide folding (Roit, supra).

The alternative approach to preparing proteins for vaccines involves the use of cloned viral DNA inserted into a suitable vector to produce viral protein in prokaryotic or eukaryotic cells (Aldovini et al., *The New Vaccines, Technology Review*, pp. 24–31, January 1992). This approach, also, has several limitations. For example, one must devise suitable conditions for the optimal production of the recombinant protein of interest by the recombinant host cells. The protein product must be isolated and purified from the culture system, and obtained in sufficient quantities for use as a vaccine. Finally, it may be necessary to perform post-translational modifications of the purified protein (such as glycosylation and/or cleavage of a fusion protein).

An alternative to producing the recombinant antigen in vitro is to introduce nucleic acid sequences coding for the antigen into the cells of the vaccinee. In this way, the antigen is produced in vivo by the vaccinee's cells and provokes the immune response. Tang et al. (*Nature* 356:152–154 (1992)) have shown that it is possible produce an immune response to human growth hormone protein in mice by propelling gold microprojectiles coated with plasmids containing human growth hormone genomic sequences. The resultant variability in the production of antibody production was hypothesized to arise from the operation of the microprojectile device, or the coating of the DNA onto the microprojectiles.

More recently, Ulmer et al. (*Science* 259:1745–1749 (1993)) injected a plasmid carrying the gene for influenza A nucleoprotein into the quadriceps of mice. The mice produced nucleoprotein antibodies, indicating that the gene was expressed in murine cells. The mice also produced nucleoprotein-specific cytotoxic T lymphocytes which were effective in protecting the mice from a subsequent challenge with a heterologous strain of influenza A virus. Similarly, Wang et al. (*Proc. Natl. Acad. Sci. USA* 90:4156–4160 (1993)) observed that the intramuscular injection of a human immunodeficiency virus (HIV) type 1 envelope DNA construct in mice generated antigen-specific cellular and humoral immune responses. In addition, splenic lymphocytes derived from the inoculated mice demonstrated HIV-envelope-specific proliferative responses. Thus, direct inoculation of DNA coding for pathogenic antigens can provide an alternative to the use of viruses, proteins, or peptides.

One problem with using naked DNA for inoculation is the low efficiency of cellular uptake. For example, the protocol of Wang et al., supra, requires the injection of 100 μg of the DNA construct biweekly for a total of four inoculations. As described herein, the use of cationic lipids as a carrier for DNA constructs provides a more efficient means of genetic immunization. According to the present invention, genetic immunization can be achieved with as little as 5 μg of a DNA construct, which has been complexed with cationic lipid.

Liposomes have been used as carriers of genetic information in the transfection of tissue culture cells. A fundamental problem of liposome-mediated transfection with liposomes comprising neutral or anionic lipids is that such liposomes do not generally fuse with the target cell surface. Instead, the liposomes are taken up phagocytically, and the polynucleotides are subsequently subjected to the degradative enzymes of the lysosomal compartment (Straubinger et al., *Methods Enzymol.* 101:512–527 (1983); Mannino et al., *Biotechniques* 6:682–690 (1988)). Another problem with conventional liposome technology is that the aqueous space of typical liposomes may be too small to accommodate large macromolecules such as DNA or RNA. As a result, typical liposomes have a low efficiency (Felgner, "Cationic Liposome-Mediated Transfection with Lipofectin™ Reagent," in *Gene Transfer and Expression Protocols Vol. 7*, Murray, E. J. Ed., Humana Press, New Jersey, pp. 81–89 (1991)).

Liposomes comprising cationic lipids interact spontaneously and rapidly with polyanions such as DNA and RNA, resulting in liposome/nucleic acid complexes that capture 100% of the polynucleotide (Felgner et al., *Proc. Natl. Acad. Sci. U.S.A.* 84:7413–7417 (1987); Felgner et al., *Focus* 11:21–25 (1989)). Moreover, the polycationic complexes are taken up by the anionic surface of tissue culture cells with an efficiency that is about ten to one hundred times greater than negatively charged or neutral liposomes (Felgner, "Cationic Liposome-Mediated Transfection with Lipofectin™ Reagent," in *Gene Transfer and Expression Protocols Vol. 7*, Murray, E. J., Ed., Humana Press, New Jersey, pp. 81–89 (1991)). In addition, the polycationic complexes fuse with cell membranes, resulting in an intracellular delivery of polynucleotide that bypasses the degradative enzymes of the lysosomal compartment (Düzgünes et al., *Biochemistry* 28:9179–9184 (1989); Felgner et al., *Nature* 337:387–388 (1989)).

Various formulations of cationic lipids have been used to transfect cells in vitro (WO 91/17424; WO 91/16024; U.S. Pat. Nos. 4,897,355; 4,946,787; 5,049,386; and 5,208,036). Cationic lipids have also been used to introduce foreign polynucleotides into frog and rat cells in vivo (Holt et al., *Neuron* 4:203–214 (1990); Hazinski et al., *Am. J. Respr. Cell. Mol. Biol.* 4:206–209 (1991)). Therefore, cationic lipids may be used, generally, as pharmaceutical carriers to provide biologically active substances (for example, see WO 91/17424; WO 91/16024; and WO 93/03709). Thus, cationic liposomes can provide an efficient carrier for the introduction of foreign polynucleotides into host cells for genetic immunization.

Various cationic lipids are well-known in the prior art. One well-known cationic lipid is N-[1-(2,3-dioleoyloxy) propyl]-N,N,N-trimethylammonium chloride (DOTMA). The structure of DOTMA is:

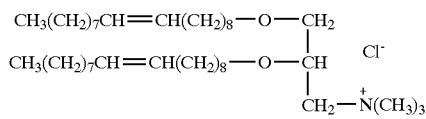

DOTMA, alone or in a 1:1 combination with dioleoylphosphatidylethanolamine (DOPE) can be formulated into liposomes using standard techniques. Felgner et al. (*Proc. Natl. Acad. Sci. U.S.A.* 84:7413–7417 (1987)) have shown that such liposomes provide efficient delivery of nucleic acids to cultured cells. A DOTMA:DOPE (1:1) formulation is sold under the name LIPOFECTIN™ (GIBCO/BRL: Life Technologies, Inc., Gaithersburg, Md.). Another commercially available cationic lipid is 1,2-bis(oleoyloxy)-3-3-(trimethylammonia)propane (DOTAP), which differs from DOTMA in that the oleoyl moieties are linked via ester bonds, not ether bonds, to the propylamine. DOTAP is believed to be more readily degraded by target cells.

A related groups of known compounds differ from DOTMA and DOTAP in that one of the methyl groups of the trimethylammonium group is replaced by a hydroxyethyl group. Compounds of this type are similar to the Rosenthal Inhibitor of phospholipase A (Rosenthal et al., *J. Biol. Chem.* 235:2202–2206 (1960), which has stearoyl esters linked to the propylamine core. The dioleoyl analogs of the Rosenthal Inhibitor (RI) are commonly abbreviated as DORI-ether and DORI-ester, depending upon the linkage of the fatty acid moieties to the propylamine core. The hydroxy group can be used as a site for further functionalization, for example, by esterification to carboxyspermine.

Another class of known compounds has been described by Behr et al. (*Proc. Natl. Acad. Sci. USA* 86:6982–6986 (1989); EPO Publication 0 394 111), in which carboxyspermine has been conjugated to two types of lipids. The structure of 5-carboxylspermylglycine dioctadecylamide (DOGS) is:

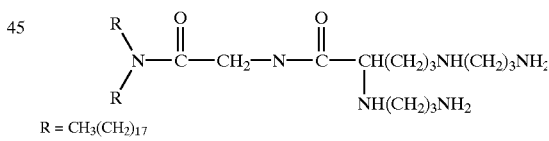

The structure of dipalmitoylphosphatidylethanolamine 5-carboxyspermylamide (DDPES) is:

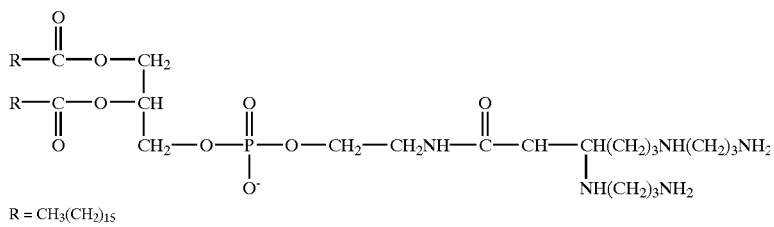

Both DOGS and DPPES have been used to coat plasmids, forming a lipid aggregate complex that provides efficient transfection. The compounds are claimed to be more efficient and less toxic than DOTMA for transfection of certain cell lines. DOGS is available commercially as TRANSFECTAM™ (Promega, Madison, Wis.).

A cationic cholesterol derivative (DC-Chol) has been synthesized and formulated into liposomes in combination with DOPE (Gao et al., *Biochim. Biophys. Res. Comm.* 179:280–285 (1991)). The structure of this compound is:

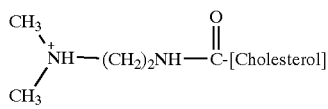

Liposomes formulated with DC-Chol provide more efficient transfection and lower toxicity than DOTMA-containing liposomes for certain cell lines.

Lipopolylysine is formed by conjugating polylysine to DOPE. This compound has been reported to be especially effective for transfection in the presence of serum (Zhou et al., *Biochim. Biophys. Res. Comm.* 165:8–14 (1991)). Thus, lipopolylysine may be an effective carrier for immunization.

In addition, Gebeyhu et al. (co-pending U.S. application Ser. No. 07/937,508; filed Aug. 28, 1992) have developed novel cationic lipids according to the general formula:

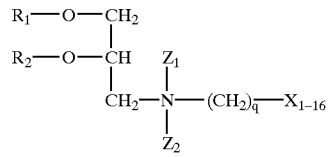

wherein $R_1$ and $R_2$ separately or together are $C_{1-23}$ alkyl or

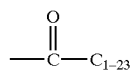

alkyl or alkenyl, q is 1 to 6,
$Z_1$ and $Z_2$ separately or together are H or unbranched alkyl $C_{1-6}$
$X_1$ is —$(CH_2)_n$Br, Cl, F or I n=0–6 or
$X_2$ is —$(CH_2)_n$NH$_2$ n=0–6 or
$X_3$ is —NH—$(CH_2)_m$—NH$_2$ m=2–6 or
$X_4$ is —NH—$(CH_2)_3$—NH—$(CH_2)_4$—NH$_2$ or
$X_5$ is —NH—$(CH_2)_3$—NH—$(CH_2)_4$—NH$(C_2)_3$—NH2

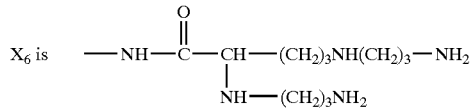

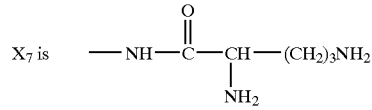

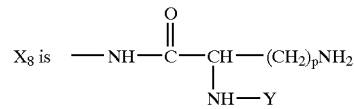

where p is 2–5, Y is H or other groups attached by amide or alkyl amino group or $X_9$ is a polyamine, e.g., polylysine, polyarginine, polybrene, histone or protamine or
$X_{10}$ is a reporter molecule, e.g.,

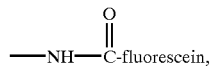

biotin, folic acid or PPD, or
$X_{11}$ is a polysaccharide or substituted polysaccharide, or
$X_{12}$ is a protein or
$X_{13}$ is an antibody or
$X_{14}$ is an amine or halide reactive group or
$X_{15}$ is —$(CH_2)_r$—SH where r is 0–6 or
$X_{16}$ is —$(CH_2)_s$—S—S—$(CH_2)_t$—NH$_2$ where s is 0–6 and t is 2–6.

These compounds are useful either alone, or in combination with other lipid aggregate-forming components (such as DOPE or cholesterol) for formulation into liposomes or other lipid aggregates. Such aggregates are cationic and able to complex with anionic macromolecules such as DNA or RNA.

SUMMARY OF THE INVENTION

The present invention is directed to a method for eliciting an immune response in an animal, comprising the steps of: (a) mixing at least one cationic lipid with a polynucleotide, coding for an antigenic determinant, thereby forming a cationic lipid-polynucleotide complex; and (b) administering the lipid-polynucleotide complex to the animal.

The present invention is also directed to a method for generating active immunity against an infectious disease in an animal, comprising the steps of: (a) mixing at least one cationic lipid with a polynucleotide, coding for an antigenic determinant of an organism which is the causative agent of the infectious disease, thereby forming a cationic lipid-polynucleotide complex; and (b) administering the lipid-polynucleotide complex to the animal; whereby active immunity to the infectious disease is generated.

The present invention is also directed to such a genetic immunization method wherein the polynucleotide is an expression vector comprising a DNA sequence coding for an immunogen, wherein the transcription of the DNA sequence is under the control of a promoter.

The present invention is further directed to a genetic immunization method wherein the polynucleotide is an RNA molecule which codes for an immunogen.

The present invention is further directed to a method for producing polyclonal antibodies comprising the use of the genetic immunization method described above, and further comprising the step of isolating the polyclonal antibodies from the immunized animal.

The present invention is also directed to a method for producing monoclonal antibodies comprising the steps of:
(a) mixing at least one cationic lipid with a polynucleotide thereby forming a lipid-polynucleotide complex, wherein the polynucleotide comprises a DNA sequence coding for an immunogen;
(b) administering the lipid-polynucleotide complex to at least one mouse;
(c) removing B-lymphocytes from the immunized mice;
(d) fusing the B-lymphocytes from the immunized mice with myeloma cells, thereby producing hybridomas;
(e) cloning the hybridomas;
(f) selecting positive clones which produce anti-immunogen antibody;

(g) culturing the anti-immunogen antibody-producing clones; and (h) isolating anti-immunogen antibodies from the cultures.

The present invention is also directed to a method for mapping the epitopes of a protein molecule, comprising the steps of:

(a) fragmenting DNA molecules coding for the protein in a random manner;

(b) subcloning the DNA fragments in an expression vector;

(c) mixing at least one cationic lipid with each expression vector subclone, thereby forming a cationic lipid-expression vector complex with each expression vector subclone;

(d) administering the cationic lipid-expression vector complexes to mice; and (d) determining which of the DNA fragments are capable of generating the production of antibodies in the mice.

Definitions

In the description that follows, a number of terms used in recombinant DNA technology are utilized extensively. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Recombinant Host. In general, a recombinant host may be any prokaryotic or eukaryotic microorganism or cell which contains the desired cloned genes on an expression vector or cloning vector. This term is also meant to include those microorganisms that have been genetically engineered to contain the desired gene(s) in the chromosome or genome of that organism.

Recombinant vector. Any cloning vector or expression vector which contains the desired cloned gene(s).

Host. Any prokaryotic or eukaryotic microorganism or cell that is the recipient of a replicable expression vector or cloning vector. A "host," as the term is used herein, also includes prokaryotic or eukaryotic microorganisms or cells that can be genetically engineered by well known techniques to contain desired gene(s) on its chromosome or genome. For examples of such hosts, see Maniatis et al., *Molecular Cloning: A Laboratory Manual*, Cold Spring Harbor Laboratory, Cold Spring Harbor, N.Y. (1982).

Promoter. A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Gene. A DNA sequence that contains information needed for expressing a polypeptide or protein.

Structural gene. A DNA sequence that is transcribed into messenger RNA (mRNA) that is then translated into a sequence of amino acids characteristic of a specific polypeptide.

Expression. Expression is the process by which a polypeptide is produced from a structural gene. The process involves transcription of the gene into mRNA and the translation of such mRNA into polypeptide(s).

Transfection. Transfection refers to the transformation of a host cell with DNA. The recombinant host cell expresses protein which is encoded by the transfected DNA.

Epitope. The part of a non-immunoglobulin antigen to which the variable region of an antibody binds.

Antigenic Determinant. A protein or peptide which contains one or more epitopes.

Immunogen. A protein or peptide which is capable of eliciting an immune response due to the presence of one or more epitopes.

DETAILED DESCRIPTION OF THE INVENTION

The present invention is directed to a method for eliciting an immune response in an animal by administering a cationic lipid-polynucleotide complex, wherein the polynucleotide codes for an antigenic determinant.

The present invention is also directed to a method for generating active immunity against an infectious disease in an animal by administering a cationic lipid-polynucleotide complex, wherein the polynucleotide codes for an antigenic determinant of an organism which is the causative agent of the infectious disease.

The present invention is also directed to such a genetic immunization method wherein the polynucleotide is an expression vector comprising a DNA sequence coding for an immunogen, wherein the transcription of the DNA sequence is under the control of a promoter.

The present invention is further directed to a genetic immunization method wherein the polynucleotide is an RNA molecule which codes for an immunogen.

The present invention is further directed to a method for producing polyclonal antibodies comprising the use of the genetic immunization method described above, and further comprising the step of isolating the polyclonal antibodies from the immunized animal.

The present invention is also directed to a method for producing monoclonal antibodies using B-lymphocytes from mice following genetic immunization.

The present invention is also directed to a method for epitope mapping using genetic immunization.

I. Cationic Liposomes

Any of the cationic lipids known in the prior art may be employed in the practice of the claimed invention. See, for example, Felgner et al. (*Proc. Natl. Acad. Sci. U.S.A.* 84:7413–7417 (1987)); Felgner et al. (*Focus* 11:21–25 (1989)); Felgner ("Cationic Liposome-Mediated Transfection with Lipofectin™ Reagent," in *Gene Transfer and Expression Protocols Vol. 7*, Murray, E. J., Ed., Humana Press, New Jersey, pp. 81–89 (1991)); WO 91/17424; WO 91/16024; U.S. Pat. Nos. 4,897,355; 4,946,787; 5,049,386; 5,208,036; Behr et al. (*Proc. Natl. Acad. Sci. USA* 86:6982–6986 (1989); EPO Publication 0 394 111); Gao et al. (*Biochim. Biophys. Res. Comm.* 179:280–285 (1991)); Zhou et al., (*Biochim. Biophys. Res. Comm.* 165:8–14 (1991)); and Gebeychu et al. (co-owned U.S. application Ser. No. 07/937,508; filed Aug. 28, 1992), the contents of which are fully incorporated by reference.

Preferred cationic lipids include N-[1-(2,3-dioleoyloxy) propyl]-N,N,N-trimethylammonium chloride (DOTMA). The structure of DOTMA is:

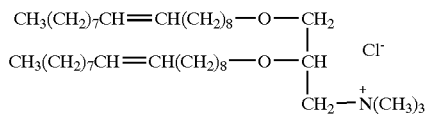

DOTMA, alone or in a 1:1 combination with dioleoylphosphatidylethanolamine (DOPE) can be formulated into liposomes using standard techniques. A DOTMA:DOPE (1:1) formulation is sold under the name LIPOFECTIN™ (GIBCO/BRL: Life Technologies, Inc., Gaithersburg, Md.).

Another preferred commercially available cationic lipid is 1,2-bis(oleoyloxy)-3-3-(trimethylammonia)propane (DOTAP), which differs from DOTMA in that the oleoyl moieties are linked via ester bonds, not ether bonds, to the propylamine.

A related group of preferred cationic lipids differ from DOTMA and DOTAP in that one of the methyl groups of the trimethylammonium group is replaced by a hydroxyethyl group. Compounds of this type are similar to the Rosenthal Inhibitor of phospholipase A (Rosenthal et al., supra), which has stearoyl esters linked to the propylamine core. The dioleoyl analogs of the Rosenthal Inhibitor (RI) are commonly abbreviated as DORI-ether and DORI-ester, depending upon the linkage of the fatty acid moieties to the propylamine core. The hydroxy group can be used as a site for further functionalization, for example, by esterification to carboxyspermine.

In another class of preferred cationic lipids, carboxyspermine has been conjugated to two types of lipids. The structure of 5-carboxylspermylglycine dioctadecylamide (DOGS) is:

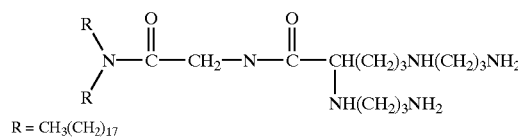

The structure of dipalmitoylphosphatidylethanolamine 5-carboxyspermylamide (DDPES) is:

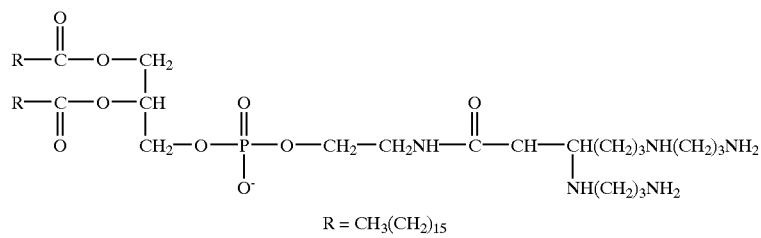

DOGS is available commercially as TRANSFECTAM™ (Promega, Madison, Wis.).

Another preferred cationic lipid is a cholesterol derivative (DC-Chol) which has been synthesized and formulated into liposomes in combination with DOPE. The structure of this compound is:

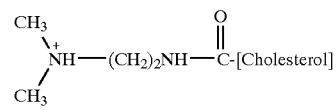

Another preferred cationic lipid is lipopolylysine, which is formed by conjugating polylysine to DOPE.

Additional preferred cationic lipids are described by the general formula:

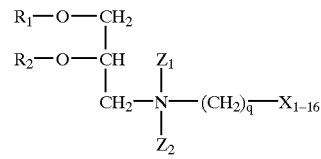

wherein $R_1$ and $R_2$ separately or together are $C_{1-23}$ alkyl or

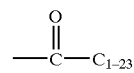

alkyl or alkenyl, q is 1 to 6, $Z_1$ and $Z_2$ separately or together are H or unbranched alkyl $C_{1-6}$ $X_1$ is —$(CH_2)_n$Br, Cl, F or I n=0–6 or $X_2$ is —$(CH_2)_n NH_2$ n=0–6 or $X_3$ is —NH—$(CH_2)_m$—$NH_2$ m=2–6 or $X_4$ is —NH—$(CH_2)_3$—NH—$(CH_2)_4$—$NH_2$ or $X_5$ is —NH—$(CH_2)_3$—NH—$(CH_2)_4$—NH$(CH_2)_3$—NH2

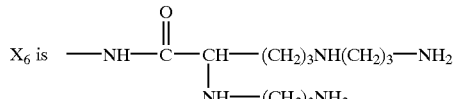

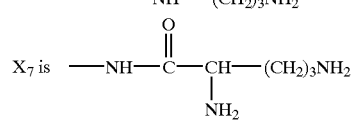

-continued

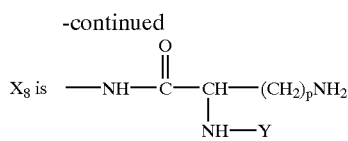

where p is 2–5, Y is H or other groups attached by amide or alkyl amino group or $X_9$ is a polyamine, e.g., polylysine, polyarginine, polybrene, histone or protamine or $X_{10}$ is a reporter molecule, e.g.,

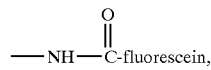

biotin, folic acid or PPD, or $X_{11}$ is a polysaccharide or substituted polysaccharide, or
$X_{12}$ is a protein or
$X_{13}$ is an antibody or
$X_{14}$ is an amine or halide reactive group or
$X_{15}$ is —$(CH_2)_r$—SH where r is 0–6 or
$X_{16}$ is —$(CH_2)_s$—S—S—$(CH_2)_t$—$NH_2$ where s is 0–6 and t is 2–6.

These compounds are useful either alone, or in combination with other lipid aggregate-forming components (such as DOPE or cholesterol) for formulation into liposomes or other lipid aggregates. Such aggregates are cationic and able to complex with anionic macromolecules such as DNA or RNA.

II. Expression Vectors

One form of polynucleotide which can be used for genetic immunization is a plasmid expression vector for the expression of the immunogen protein in eukaryotic cells. The eukaryotic expression vector comprises four main components. First, the plasmid must contain prokaryotic sequences which code for a bacterial replication origin and an antibiotic resistance marker. These prokaryotic sequences allow the propagation and selection of the plasmid within the bacterial host. Second, the plasmid must contain eukaryotic elements which control initiation of transcription. These elements include promoter and, possibly, enhancer sequences. Third, the plasmid must contain sequences involved in the processing of transcripts, such as polyadenylation sequences. Fourth, the plasmid must contain DNA sequences coding for the immunogen. These DNA sequences may be either genomic DNA sequences, or complementary DNA (cDNA) sequences. (For reviews of expression vectors, see Old et al., supra; Sambrook et al., *Molecular Cloning: A Laboratory Manual*, 2nd Edition, Cold Spring Harbor Laboratory Press, 1989; Gorman, "High Efficiency Gene Transfer into Mammalian Cells," in *DNA Cloning, Volume II*, Glover, D. M., Ed., IRL Press, Washington, D.C., pp. 143–190 (1985).)

DNA or cDNA molecules which encode an immunogen can be operably linked into the expression vector. Two DNA sequences (such as a promoter region sequence and an immunogen encoding sequence) are said to be operably linked if the nature of the linkage between the two DNA sequences does not (1) result in the introduction of a frame-shift mutation, (2) interfere with the ability of the promoter region sequence to direct the transcription of the immunogen encoding gene sequence, or (3) interfere with the ability of the immunogen gene sequence to be transcribed by the promoter region sequence.

A DNA sequence encoding an immunogen molecule may be recombined with vector DNA in accordance with conventional techniques, including blunt-ended or stagger-ended termini for ligation, restriction digestion to provide appropriate termini, filling in of cohesive ends as appropriate, alkaline phosphatase treatment to avoid undesirable joining, and ligation with appropriate ligases.

A wide variety of transcriptional and translational regulatory sequences may be employed, depending upon the nature of the host. For a mammalian host, the transcriptional and translational regulatory signals may be derived from viral sources, such as adenovirus, bovine papilloma virus, simian virus, or the like, where the regulatory signals are associated with a particular gene which has a high level of expression. In addition, promoters from mammalian expression products, such as actin, collagen, myosin, etc., may be employed. Alternatively, a prokaryotic promoter (such as the bacteriophage T3 RNA polymerase promoter) may be employed, wherein the prokaryotic promoter is regulated by a eukaryotic promoter (for example, see Zhou et al., *Mol. Cell. Biol.* 10:4529–4537 (1990); Kaufman et al., *Nucl. Acids Res.* 19:4485–4490 (1991)). Transcriptional initiation regulatory signals may be selected which allow for repression or activation, so that expression of the genes can be modulated.

The expression of the desired immunogen molecule in animals requires the use of eukaryotic regulatory regions. Such regions will, in general, include a promoter region sufficient to direct the initiation of RNA synthesis. Preferred eukaryotic promoters include the promoter of the mouse metallothionein I gene (Hamer et al., *J. Mol. Appl. Gen.* 1:273–288 (1982)); the TK promoter of Herpes virus (McKnight, S., *Cell* 31:355–365 (1982)); the SV40 early promoter (Benoist et al., *Nature* (*London*) 290:304–310 (1981)); the Rous sarcoma virus promoter (Gorman et al., supra); and the cytomegalovirus promoter (Foecking et al., *Gene* 45:101 (1980)).

As is widely known, translation of eukaryotic mRNA is initiated at the codon which encodes the first methionine. For this reason, it is preferable to ensure that the linkage between a eukaryotic promoter and a DNA sequence which encodes the desired immunogen molecule does not contain any intervening codons which are capable of encoding a methionine (i.e., AUG). The presence of such codons results either in the formation of a fusion protein (if the AUG codon is in the same reading frame as the desired receptor molecule encoding DNA sequence) or a frame-shift mutation (if the AUG codon is not in the same reading frame as the desired receptor molecule encoding sequence).

The desired immunogen molecule encoding sequence and an operably linked promoter may be introduced into the cells of the vaccinee either as a non-replicating DNA (or RNA) molecule, which may either be a linear molecule or, more preferably, a closed covalent circular molecule. Since such molecules are incapable of autonomous replication, the expression of the desired receptor molecule may occur through the transient expression of the introduced sequence. Alternatively, permanent expression may occur through the integration of the introduced sequence into the host chromosome.

Preferably, the introduced sequence will be incorporated into a plasmid or viral vector capable of autonomous replication in the recipient host. Several possible vector systems are available for this purpose. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Additional elements may also be needed for optimal synthesis of mRNA. These elements may include splice signals, as well as transcription promoters, enhancers, and termination signals. The cDNA expression vectors incorporating such elements include those described by Okayama, *Mol. Cell. Biol.* 3:280 (1983), and others.

Alternatively, the polynucleotide molecule can be an RNA molecule which codes for the desired immunogen. Sufficient quantities of such RNA molecules may be obtained using in vitro transcription, followed by RNA purification. The technique of transcribing cloned DNA sequences in vitro using DNA-dependent RNA polymerases is well-known in the art (for example, see Sambrook et al., supra).

Any immunogen-encoding sequence can be used in this invention. For example, such immunogens include herpes simplex virus glycoprotein D, hepatitis B surface antigen, influenza virus haemagglutinin, and human immunodeficiency virus envelope antigen. In addition, the claimed invention may be used to characterize the protein product of a polynucleotide sequence of unknown identity, as described below.

III. Use of the Lipid/Polynucleotide Complex

According to the present invention, the lipid/polynucleotide complex is used to carry out an in vivo transfection. Transfected cells express the protein encoded by the polynucleotide, and may present the foreign protein on the cell surface. As a result, the host animal mounts an immune response to the foreign protein, or immunogen.

Thus, the lipid/polynucleotide complex can be used as a vaccine to induce active immunity. Preferably, such active immunity is induced in humans, although the invention is not intended to be so limiting. Any animal which may experience the beneficial effects of the vaccines of the invention are within the scope of animals which may be treated according to the claimed invention.

Genetic immunization may be performed by administering vaccines comprising the cationic lipid and polynucleotide in a wide range of dosages, and over a wide range of ratios. Effective dosages and formulations will depend upon a variety of factors (such as the species of the vaccinee), and can be determined by one of ordinary skill in the art. Illustrative dosages, formulations, and modes of administration are provided below.

Cationic lipid-polynucleotide complexes are formed by mixing a cationic lipid solution with an equal volume of polynucleotide solution. The cationic lipid and polynucleotides can be dissolved in any sterile physiologically-compatible aqueous carrier. Preferably, cationic lipid and polynucleotides are dissolved in sterile saline (150 mM NaCl). The solutions are mixed at ambient temperatures. Preferably, the solutions are mixed at 25° C. After mixing, the cationic lipid-polynucleotide complexes are incubated at room temperature, preferably for 15 to 45 minutes.

Administration of lipid/polynucleotide complexes of the present invention may be by parenteral, intravenous, intramuscular, subcutaneous, intranasal, or any other suitable means. The specific dosage administered may be dependent upon the age, weight, kind of current treatment, if any, and nature of the immunogen which will be expressed. The initial dose may be followed by a booster dosage after a period of about four weeks to enhance the immunogenic response.

Since genetic immunization generates the production of immunogen-specific antibodies in the vaccinee, the present invention is also directed to methods of producing immunogen-specific antibodies. Polyclonal antibodies may be isolated and purified from vaccinated animals using procedures well-known in the art (for example, see Harlow et al., *Antibodies: A Laboratory Manual*, Cold Spring Harbor Laboratory Press, 1988).

This invention is also directed to the use of genetic immunization to produce monoclonal antibodies. According to this method, mice are injected with a lipid/polynucleotide complex, and B-lymphocytes are isolated from the immunized mice. Monoclonal antibodies are produced following the procedure of Köhler and Milstein (*Nature* 256:495–497 (1975) (for example, see Harlow et al., supra). Briefly, monoclonal antibodies can be produced by immunizing mice with a cationic lipid-polynucleotide complex, verifying the presence of antibody production by removing a serum sample, removing the spleen to obtain B-lymphocytes, fusing the B-lymphocytes with myeloma cells to produce hybridomas, cloning the hybridomas, selecting positive clones which produce anti-immunogen antibody, culturing the anti-immunogen antibody-producing clones, and isolating anti-immunogen antibodies from the hybridoma cultures.

As an alternative to generating monoclonal antibodies to known immunogens, genetic immunization can be used to identify antigenic determinants in a protein by epitope mapping. According to this method, the polynucleotide of the lipid/polynucleotide complex codes for a portion of a protein molecule. Preferably, random fragments of the DNA encoding the complete protein molecule are generated using sonication (Deininger et al., *Anal. Biochem.* 129:216–223 (1983)) or partial DNase I digestion (Anderson et al., *Nucleic Acids Res.* 9:3015–3027 (1981)), and cloned by blunt-end ligation into a suitable site of an expression vector. Alternatively, DNA fragments for epitope mapping can be obtained by treating DNA molecules with one or more restriction endonucleases, or by using the polymerase chain reaction to synthesize DNA molecules. The generation of monoclonal antibodies by cells derived from the immunized mice will indicate which segments of the protein molecule are immunogenic.

In addition, the claimed invention may be used to characterize the protein product encoded by a DNA or RNA sequence of unknown identity. For example, a genomic library can be constructed in a cosmid vector, wherein the expression of the cloned DNA fragments is regulated by a promoter. The genetic immunization technique can then be used to immunologically characterize the protein products of the subcloned genomic fragments.

As described above, genetic immunization protocols in which naked DNA is administered can require as much as 100 µg of a DNA construct per inoculation. In contrast, the use of cationic lipids as a carrier for DNA constructs according to the claimed invention permits genetic immunization with as little as 5 µg of a DNA construct. Thus, the claimed invention provides a more efficient means of genetic immunization.

Having now generally described the invention, the same will be more readily understood through reference to the following examples which are provided by way of illustration, and are not intended to be limiting of the present invention, unless specified.

EXAMPLE 1

Evaluation of the Immunization Protocol

This series of experiments employed pSV2CAT plasmids which carry the bacterial chloramphenicol acetyl transferase (CAT) gene under the control of the simian virus 40 promoter (SV; Gorman, "High Efficiency Gene Transfer into Mammalian Cells," in *DNA Cloning, Volume II*, Glover, D. M., Ed., IRL Press, Washington, D.C., pp. 143–190 (1985)). Plasmid DNA was isolated from bacterial cells by the alkaline lysis method, and purified by isopycnic centrifugation in cesium chloride/ethidium bromide gradients (Maniatis et al., supra). These experiments employed LIPO-FECTAMINE™ (BRL) as the cationic lipid. LIPO-FECTAMINE™ is composed of 2,3-dioleyloxy-N-[2 (sperminecarboxamido)ethyl]-N,N-dimethyl-1-propanaminium trifluoroacetate (DOSPA), which is formulated with dioleoylphosphatidyl ethanolamine (DOPE) at a 3:1 (W:W) ratio in water. The cationic lipids and plasmids were dissolved in sterile saline (150 mM NaCl).

Lipid/DNA complexes were administered to mice by intraperitoneally (IP) or intranasally (IN). For IN administration, lipid/DNA mixtures were formed by mixing 25 µl of a DNA solution with 25 µl of a lipid solution. For IP administration, lipid/DNA mixtures were formed by mixing 200 µl of a DNA solution with 200 µl of a lipid solution. In these experiments, 5 µg of pSV2CAT were mixed with 0, 15, 30, 45, or 60 µg of lipid. After mixing, the lipid/DNA complexes were allowed to sit at room temperature for 15–45 minutes before administration. As a control, certain mice were injected subcutaneously (SC) with CAT protein (25 µg) in complete Freund's adjuvant.

A CAT enzyme-linked immunoassay (ELISA) was used to determine the presence of CAT antibodies in mouse sera samples. Microwell titer plates were prepared by incubating each well of the plate with 1 µg/ml of CAT in 0.1 M sodium carbonate buffer, pH 9.5. The plates were incubated for 18 hours at 4° C. The wells were blocked with 0.2% ovalbumin dissolved in phosphate-buffered saline (PBS) with 0.1% Tween-20 (dilution buffer). Samples were diluted in the dilution buffer, and 200 µl were added to a well on the plate. The plate was sealed, and then incubated for 60 minutes at 37° C. Following a wash, the plates were incubated with 0.1 µg/ml goat anti-mouse IgG—horseradish peroxidase (HRP) conjugate. The plate was sealed and then incubated for 30 minutes at 37° C. Following a second wash, the plates were developed with 3,3',5,5'-tetramethylbenzidine substrate at room temperature. The reaction was stopped by adding 2N sulfuric acid.

Mice which were immunized with lipid/CAT protein developed an immune response, although it was not as great as the response generated by administration of CAT protein in complete Freund's adjuvant. Several mice injected IP with lipid/pSV2CAT generated an immune response which was weak, but clearly above background. Immunization by intranasal administration gave results that varied among mice, but with a response that was greater than that seen with IP administration.

EXAMPLE 2

Comparison of Cationic Lipids as DNA Complexing Agents

These experiments compared the following cationic lipids: LIPOFECTAMINE™, LIPOFECTACE™ (BRL), DORI-ether (VICAL, Inc., San Diego, Calif.), DORI-ether/lysolipid (VICAL Inc., San Diego, Calif.), and a bromolipid (1-propanaminium, N-[2(2-bromo)ethyl]-N,N-dimethyl-2, 3-bis(9-octadecenyloxy)-bromide). LIPOFECTACE™ is a 1:2.5 (W/W) liposome formulation of dimethyldioctadecylammonium bromide (DDAB) and dioleoylphosphatidylethanolamine (DOPE). The bromo lipid was prepared as described in co-pending U.S. application Ser. No. 07/937, 508 (filed Aug. 28, 1992), which is fully incorporated by reference.

Immunizations were performed by using IP administration of 5, 10, 20, 40, or 80 µg of pSV2CAT, which was complexed with a cationic lipid in a 1:4 ratio (W/W; pSV2CAT/cationic lipid). One mouse received pSV2CAT only, one mouse received CAT protein only, and one mouse received CAT protein in complete Freund's adjuvant. At about day 14, selected mice were given a booster shot.

The results were analyzed using Western Blot analysis. Nitrocellulose sheets were prepared by applying purified CAT protein to the nitrocellulose (0.1 µg CAT protein/cm nitrocellulose). Sera samples were diluted into dilution buffer and 2 ml were added to each nitrocellulose strip. The strips were incubated for 90 minutes with rocking at room temperature. Following a wash, the strips were incubated with 0.1 µg/ml goat anti-mouse IgG-alkaline phosphatase conjugate. The strips were then incubated for 30 minutes at room temperature. The strips were developed with 1 ml of nitroblue tetrazolium/5-bromo-4-chloro-3-indoyl phosphate stable mix substrate. The strips were rinsed with distilled water following development and dried.

The results demonstrated that mice immunized with DNA and lipid produced anti-CAT antibodies. The booster shot did not seem to greatly enhance the response. Western blot analysis showed that although the ELISA results indicated different intensities of immune response, all the animals injected with lipid-DNA complexes generated anti-CAT IgG.

EXAMPLE 3

Effect of Different Promoters on the Immune Response

These experiments used the bromo lipid (described in Example 2) or LIPOFECTACE™ as the cationic lipid. The CAT plasmids comprised either the cytomegalovirus (CMV) promoter (Foecking et al., *Gene* 45:101 (1980)), the Rous sarcoma virus (RSV) promoter (Gorman, "High Efficiency Gene Transfer into Mammalian Cells," in *DNA Cloning, Volume II*, Glover, D. M., Ed., IRL Press, Washington, D.C., pp. 143–190 (1985)), or the SV40 promoter (described above). Mice were immunized IP, as described above, following the protocol:

| Lipid | Lipid quantity | DNA quantity |
| --- | --- | --- |
| Bromo Lipid | 20 µg | 5 µg |
| or | 40 µg | 10 µg |
| LIPOFECTACE ™ | 80 µg | 20 µg |

One set (i.e., two mice) were used to test each promoter. As controls, mice received DNA without lipid, CAT protein in complete Freund's adjuvant, or no inoculation.

The results of ELISA analysis indicated that the SV40 promoter seemed to work the best followed by the CMV promoter and then, the RSV promoter. The bromo lipid gave more consistent results, compared with LIPOFECTACE™, in generating an immune response. The positive results observed in the ELISA was confirmed by Western Blot analysis. In both assay formats, the results obtained with DNA-lipid immunizations were greater than the results observed with DNA alone.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following Claims.

All publications and patent applications mentioned in this specification are indicative of the level of skill of those in the art to which the invention pertains. All publications and patent applications are herein incorporated by reference to the same extent as if each individual publication or patent application was specifically and individually indicated to be incorporated by reference in their entirety.

What is claimed is:

1. A method for producing polyclonal antibodies to an immunogen in a non-human animal, comprising:
   (a) mixing at least one cationic lipid with a polynucleotide coding for said immunogen, thereby forming a cationic lipid-polynucleotide complex;
   (b) administering said cationic lipid-polynucleotide complex to said animal; and
   (c) isolating said polyclonal antibodies from said animal.

2. The method as in claim 1, wherein said polynucleotide is a recombinant RNA molecule comprising:
   (a) a regulatory sequence; and
   (b) an RNA sequence coding for said immunogen, wherein the expression of said RNA sequence is under the control of said regulatory sequence.

3. The method according to claim 2, wherein said regulatory sequence is a viral, prokaryotic or mammalian regulatory sequence.

4. The method according to claim 2, wherein said regulatory sequence comprises a promoter sequence capable of regulating expression of said RNA sequence.

5. The method of claim 1, wherein said polynucleotide is a recombinant DNA molecule comprising:
   (a) a regulatory sequence; and
   (b) a DNA sequence coding for said immunogen, wherein the transcription of said DNA sequence is under the control of said regulatory sequence.

6. The method according to claim 5, wherein said regulatory sequence is a viral, prokaryotic or mammalian regulatory sequence.

7. The method according to claim 5, wherein said regulatory sequence comprises a promoter sequence capable of regulating expression of said DNA sequence.

8. The method of claim 7, wherein said promoter is an SV40 promoter.

9. The method of claim 7, wherein said promoter is an RSV promoter.

10. The method of claim 7, wherein said promoter is a CMV promoter.

11. The method of claim 1, comprising administering in vivo to said animal an antibody immune response effective amount of said cationic lipid-polynucleotide complex comprising said at least one cationic lipid and said polynucleotide, wherein
   (a) said polynucleotide is expressed in said animal in sufficient amounts to elicit said antibody immune response to said immunogen;
   (b) said administering is by a parenteral, intravenous, intramuscular, subcutaneous, intranasal or intraperitoneal route; and
   (c) said cationic lipid is selected from the group consisting of (i) a cationic lipid according to formula I:

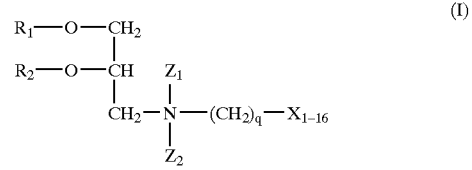

wherein $R_1$ and $R_2$ separately or together are C1–23 alkyl or

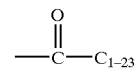

or alkyl or alkenyl;

wherein q is 1 to 6;

$Z_1$ and $Z_2$ separately or together are H or unbranched alkyl $C_{1-6}$;

$X_2$ is —$(CH_2)_n NH_2$ wherein n=0–6;

$X_3$ is —NH—$(CH_2)_m$—$NH_2$ wherein m=2–6;

$X_4$ is —NH—$(CH_2)_3$—NH—$(CH_2)_4$—$NH_2$;

$X_5$ is —NH—$(CH_2)_3$—NH—$(CH_2)_4$—NH$(CH_2)_3$—$NH_2$;

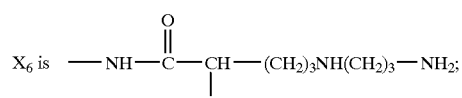

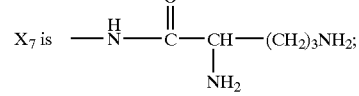

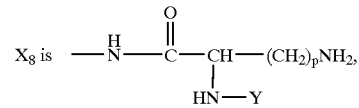

wherein p is 2–5, Y is H or an alkyl group attached by an amide or an alkyl amino group;

$X_9$ is polylysine, polyarginine, polybrene, histone or protamine;

$X_{10}$ is biotin, folic acid

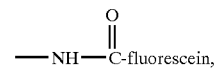

or PPD;

$X_{11}$ is a polysaccharide or substituted polysaccharide;

$X_{12}$ is a protein;

$X_{13}$ is an antibody;

$X_{14}$ is an amine;

$X_{15}$ is —$(CH_2)_r$—SH, wherein r is 0–6; and $X_{16}$ is —$(CH_2)_s$—S—S—$(CH_2)_t$—$NH_2$, wherein s is 0–6 and t is 2–6;

(ii) 5-carboxylspermylglycine dioctadecylamide (DOGS);

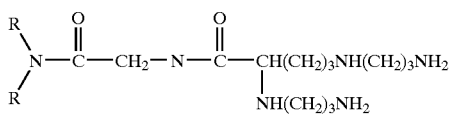

wherein R=CH$_3$(CH$_2$)$_{17}$;
(iii) dipalmitoylphosphatidylethanolamine 5-carboxyspermylamide (DPPES);

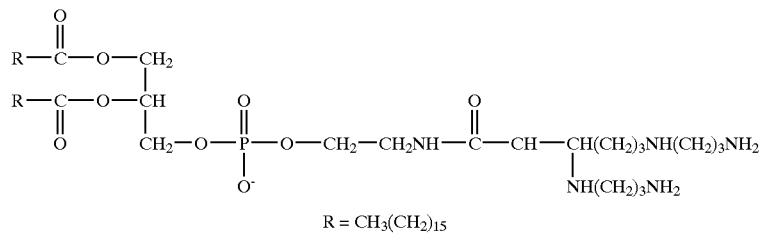

wherein R=CH$_3$(CH$_2$)$_{15}$;
(iv) a cationic cholesterol derivative (DC-Chol);

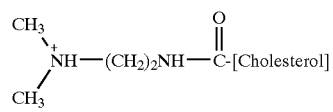

(v) a lipopolylysine;
(vi) a dioleoyl ether or ester analog of a Rosenthal inhibitor, wherein said analog is a DORI-ether having dioleoyl moieties linked by an ether linkage to a propylamine core, or a DORI-ester having dioleoyl moieties linked by an ester linkage to a propylamine core; and
(vii) a liposome formulation of dimethyldiodadecyl ammonium bromide (DDAB) and dioleoylphosphatidylethanolamine (DOPE).

12. The method according to claim 11, wherein said at least one cationic lipid comprises a cationic lipid selected from the group consisting of a trimethylammonium cationic lipid, a hydroxyethyl ammonium cationic lipid, a carboxyspermine conjugate cationic lipid, a cholesterol derivative cationic lipid, a lipopolylysine cationic lipid, and a cationic lipid compound according to formula:

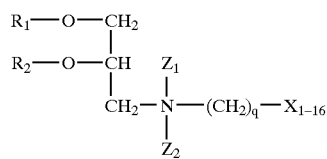

wherein R$_1$ and R$_2$ separately or together are C$_{1-23}$ alkyl or

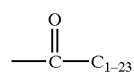

or alkyl or alkenyl;
wherein q is 1 to 6;

Z$_1$ and Z$_2$ separately or together are H or unbranched alkyl C$_{1-6}$;

X$_1$ is —(CH$_2$)$_n$Br, Cl, F or I, where n=0–6;

X$_2$ is —(CH$_2$)$_n$NH$_2$, where n=0–6;

X$_3$ is —NH—(CH$_2$)$_m$—NH$_2$, where m=2–6;

X$_4$ is —NH—(CH$_2$)$_3$—NH—(CH$_2$)$_4$—NH$_2$;

X$_5$ is —NH—(CH$_2$)$_3$—NH—(CH$_2$)$_4$—NH(CH$_2$)$_3$—NH$_2$;

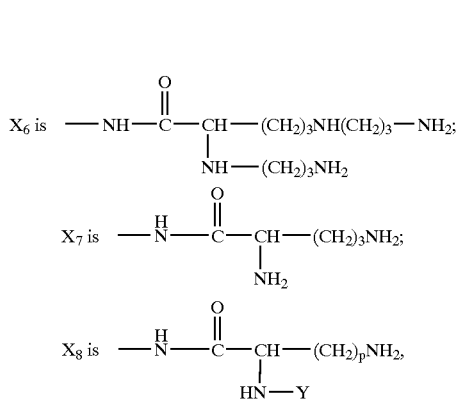

where p is 2–5, Y is H or other groups attached by amide or alkyl amino group;

X$_9$ is a polyamine;

X$_{10}$ is a reporter molecule;

X$_{11}$ is a polysaccharide or substituted polysaccharide;

X$_{12}$ is a protein;

X$_{13}$ is an antibody;

X$_{14}$ is an amine or halide reactive group;

X$_{15}$ is —(CH$_2$)$_r$—SH, where r is 0–6; and

X$_{16}$ is —(CH$_2$)$_s$—S—S—(CH$_2$)$_t$—NH2, where s is 0–6 and t is 2–6.

13. The method according to claim 12, wherein said trimethylammonium cationic lipid is selected from N-(1-(2,3-dioleoyloxy)propyl)-N,N,N-trimethylammonium chloride (DOTMA) or 1,2-bis(oleoyloxy)-3-3-(trimethylammonia) propane (DOTAP).

14. The method according to claim 12, wherein said cationic lipid is selected from the group consisting of 5-carboxyspermylglycine dioctadecylamide (DOGS) and dipalmitylphosphatidylethanolamine 5-carboxyspermylamide (DPPES).

15. The method according to claim 12, wherein said cholesterol derivative cationic lipid has the structure:

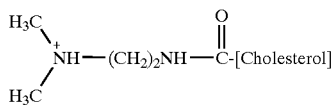
16. The method of claim 11, wherein said animal is a mouse.
17. The method of claim 11, wherein said administering is intraperitoneal.
18. The method of claim 11, wherein said administering is intranasal.
19. The method of claim 11, wherein said administering is intramuscular.
* * * * *